United States Patent
Kamimoto et al.

(10) Patent No.: US 9,498,653 B2
(45) Date of Patent: Nov. 22, 2016

(54) SUNSCREEN COSMETIC COMPOSITION CONTAINING ULTRAVIOLET ABSORBER

(75) Inventors: Tetsuo Kamimoto, Saitama (JP); Yoshinori Negishi, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 13/376,430

(22) PCT Filed: Aug. 26, 2010

(86) PCT No.: PCT/JP2010/064494
§ 371 (c)(1),
(2), (4) Date: Dec. 6, 2011

(87) PCT Pub. No.: WO2011/027710
PCT Pub. Date: Mar. 10, 2011

(65) Prior Publication Data
US 2012/0093747 A1 Apr. 19, 2012

(30) Foreign Application Priority Data
Sep. 4, 2009 (JP) .................. 2009-204961

(51) Int. Cl.
*A61Q 17/04* (2006.01)
*A61K 8/49* (2006.01)

(52) U.S. Cl.
CPC ............. *A61Q 17/04* (2013.01); *A61K 8/4966* (2013.01)

(58) Field of Classification Search
None
See application file for complete search history.

(56) References Cited

U.S. PATENT DOCUMENTS

| | | | |
|---|---|---|---|
| 6,184,375 B1 | 2/2001 | Huglin et al. | |
| 7,132,499 B2 * | 11/2006 | Tobita et al. | 528/272 |
| 2004/0228812 A1 | 11/2004 | Leblanc et al. | |
| 2006/0083696 A1 | 4/2006 | Yu et al. | |
| 2006/0183824 A1 * | 8/2006 | Hosaka et al. | 524/99 |
| 2007/0240615 A1 * | 10/2007 | Tsuda et al. | 106/287.23 |
| 2008/0138300 A2 | 6/2008 | Yu et al. | |
| 2009/0081142 A1 | 3/2009 | Omura et al. | |
| 2011/0272648 A1 | 11/2011 | Fukushima et al. | |

FOREIGN PATENT DOCUMENTS

| | | |
|---|---|---|
| DE | 3824999 | 2/1989 |
| FR | 2903008 | 1/2008 |
| GB | 2 217 987 | 11/1989 |
| JP | 5-25029 | 2/1993 |

(Continued)

OTHER PUBLICATIONS

International Search Report, PCT/JP2010/064494, Oct. 26, 2010.
(Continued)

*Primary Examiner* — Jennifer A Berrios
(74) *Attorney, Agent, or Firm* — Young & Thompson

(57) ABSTRACT

A sunscreen cosmetic composition contains an ultraviolet absorber composed of a triazine compound (a) represented by the general formula (1) below and a triazine compound (b) represented by chemical formula (2) below. In the general formula (I) below, $R_1$ represents a linear or branched $C_{1-12}$ alkyl group, a $C_{3-8}$ cycloalkyl group, a $C_{3-8}$ alkenyl group, a $C_{6-18}$ aryl group, a $C_{7-18}$ alkylaryl group, or a $C_{7-18}$ arylalkyl group (with the proviso that these groups may be substituted by a hydroxy group, a halogen atom or a $C_{1-12}$ alkyl or alkoxy group, and may be interrupted by an oxygen atom, a sulfur atom, a carbonyl group, an ester group, an amide group or an imino group, and further that the substitution and the interruption may be combined); and R2 represents a $C_{1-8}$ alkyl group, or a $C_{3-8}$ alkenyl group.

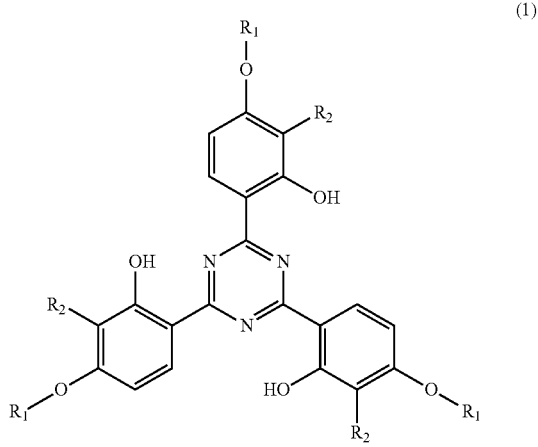

(1)

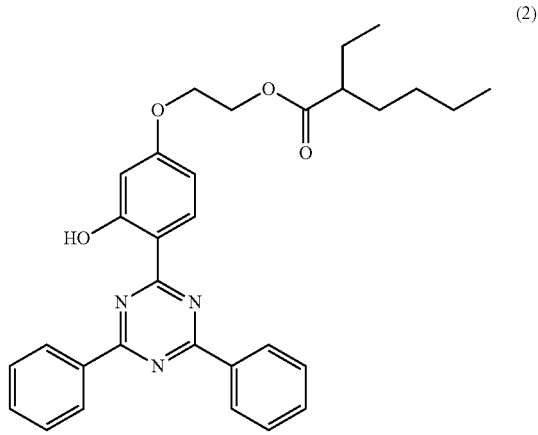

(2)

7 Claims, 1 Drawing Sheet

(56) References Cited

FOREIGN PATENT DOCUMENTS

| | | |
|---|---|---|
| JP | 11-71356 | 3/1999 |
| JP | 2001-302926 | 10/2001 |
| JP | 2004-107255 | 4/2004 |
| JP | 2004-315531 | 11/2004 |
| JP | 2006-111629 | 4/2006 |
| JP | 2006-117833 | 5/2006 |
| JP | 2007-145722 | 6/2007 |
| JP | 2008-74779 | 4/2008 |
| JP | 2009-167416 | 7/2009 |
| JP | 2009-185291 | 8/2009 |

OTHER PUBLICATIONS

Chinese Office Action dated Nov. 22, 2012 in corresponding Chinese Patent Application No. 201080024111.6 with an English translation of the Chinese Office Action.

Authors et al.: Disclose Anonymously, Stabilisation of fragrance containing personal care, body care and household products, ip.com Journal, IP ComInc, Nov. 6, 2008, pp. 13-17, 25.

\* cited by examiner

SUNSCREEN COSMETIC COMPOSITION CONTAINING ULTRAVIOLET ABSORBER

TECHNICAL FIELD

The present invention relates to a sunscreen cosmetic composition, particularly to a sunscreen cosmetic composition which absorbs short wavelengths (UV-B and UV-C) and a long wavelength (UV-A) by containing a triazine-based compound having a specific structure to protect the skin and hair from ultraviolet rays.

BACKGROUND ART

The damaging effects of sunlight on human skin have been recognized since time immemorial and many remedies have been proposed to protect the skin from this damage. In general, harmful ultraviolet (UV) rays, particularly those originating from sunlight, which penetrate the upper atmosphere and reach the earth's surface, can be classified into the following (i) and (ii).

(i) The energy-rich UV-B rays (290 to 320 nm wavelength) which possess an intense physiopathological activity on the skin. These are absorbed just above the dermis and they are responsible for erythema and skin pigmentation.

(ii) UV-A rays (320 to 400 nm wavelength) which penetrate deeper into the skin (to the dermis and beyond). Their energy is much lower than that of UV-B rays and the photobiological effects exhibited by the energy are sustained over a prolonged period of time, for example, they accelerate skin ageing.

Certain organic substances (sunscreen agents) whose molecules absorb the harmful ultra-violet rays have been proposed for use in mitigating the deleterious effects of ultraviolet radiation. Some of these substances absorb more effectively in UV-A range thereby providing a filtering effect of UV radiation in this range, while others are more effective in the UV-B range. However, a common problem exists, whatever the choice of organic sunscreen agent, for protection from any wavelength of ultra-violet radiation. This is that physiological damage to the body can occur, following topical application of these sunscreen agents in amounts necessary to provide effective filtering of harmful ultraviolet radiation. Even those organic sunscreen agents that are believed to be safe for use in this way, necessarily have safety limits imposed, based on the amount applied to the skin. As a result, sufficient protection cannot be obtained for harmful ultra-violet radiation.

Certain inorganic substances have also been proposed for use as sunscreen agents which physically prevent the skin from being exposed to ultraviolet rays. Notable among these is titanium dioxide having a very small particle size. This kind of titanium dioxide is referred to as ultrafine $TiO_2$, affords a good degree of sun blocking potential without exhibiting the unacceptable skin whitening effect observed with the normal pigmentary grade (particle size>300 nm). For example, Patent literature 1 proposes the use of titanium dioxide with an average primary particle size of <100 nm in a water-in-oil emulsion as a sunscreen preparation. Patent literature 1 suggests that organic sunscreen agents such as p-aminobenzoic acid and esters thereof, methoxycinnamate, benzophenone, dibenzoylmethane, and salicylate can also be contained to improve protection. In spite of this, and other prior proposals, there still exists a need for a sunscreen cosmetic composition which has a wide range of protection (i.e. protection for both UV-A and UV-B) in the UV region and is highly efficient and thoroughly safe.

One of the triazine-based ultraviolet absorbers to be used in the present invention is disclosed as an ultraviolet absorber for TAC films in Patent literature 2 below. The other is reported as ultraviolet absorber with large absorption in the short wavelength in Patent literature 3 below. Patent literatures 2 and 3 disclose that these triazine-based ultraviolet absorbers have ultraviolet absorption capability suitable for optical material application and are excellent in performance such as heat deterioration of synthetic resin physical properties. However, there has been no description regarding suggestion of the use of the ultraviolet absorbers for protecting the skin and hair of humans and animals from ultraviolet rays and there has been no disclosure regarding the use of the sunscreen cosmetic composition.

Patent literature 4 below discloses a sunscreen cosmetic containing a di or tri(hydroxyaryl)triazine-based compound. Further, Patent literature 5 below discloses a cosmetic dispensing containing a di(hydroxyaryl)triazine-based compound. However, an ultraviolet protective effect has not been obtained sufficiently and widely by these methods.

CITATION LIST

Patent Literature

Patent literature 1: German Patent Application No. 3,824,999

Patent literature 2: Japanese Patent Application Laid-Open (JP-A) No. 11-071356

Patent literature 3: JP-A No. 2001-302926

Patent literature 4: JP-A No. 5-025029

Patent literature 5: U.S. Pat. No. 6,184,375

DISCLOSURE OF THE INVENTION

Problems to be Solved by the Invention

An object of the present invention is to provide a sunscreen cosmetic composition which has absorption at a short wavelength side and a long wavelength side.

Means for Solving the Problem

The present inventors have conducted intensive examinations and found that a sunscreen cosmetic composition obtained by using a triazine-based compound having a specific structure can achieve the object. Further, they have found that an excellent effect which has absorption at the short and long wavelength sides, is exerted by allowing a cosmetic base material to contain the triazine-based compound having a specific structure in order to improve an ultraviolet absorption effect, and thus completed the present invention.

That is, the present invention is to provide a sunscreen cosmetic composition, containing an ultraviolet absorber composed of a triazine compound (a) represented by the general formula (1) below and a triazine compound (b) represented by chemical formula (2) below:

[Chemical formula 1]

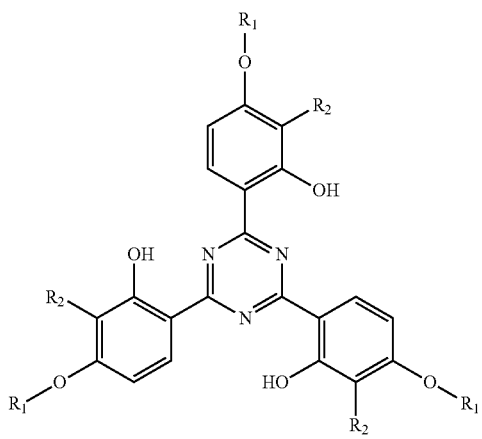

(1)

wherein $R_1$ represents a linear or branched alkyl group with 1 to 12 carbon atoms, a cycloalkyl group with 3 to 8 carbon atoms, an alkenyl group with 3 to 8 carbon atoms, an aryl group with 6 to 18 carbon atoms, an alkylaryl group with 7 to 18 carbon atoms or an arylalkyl group with 7 to 18 carbon atoms, with the proviso that the alkyl group, the cycloalkyl group, the alkenyl group, the aryl group, the alkylaryl group or the arylalkyl group may be substituted by a hydroxy group, a halogen atom, an alkyl group with 1 to 12 carbon atoms or an alkoxy group or may be interrupted by an oxygen atom, a sulfur atom, a carbonyl group, an ester group, an amide group or an imino group, further, the substitution and interruption may be combined, and $R_2$ represents an alkyl group with 1 to 8 carbon atoms or an alkenyl group with 3 to 8 carbon atoms.

[Chemical formula 2]

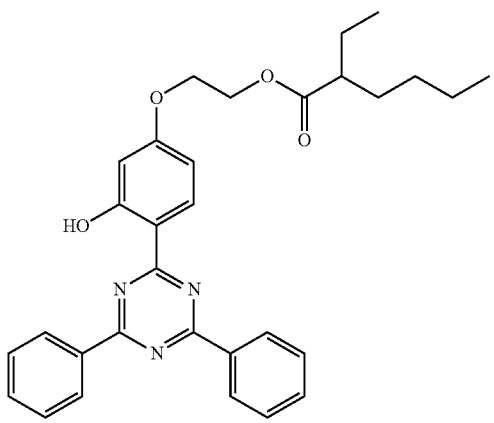

(2)

Further, the present invention is to provide a sunscreen cosmetic composition, containing an ultraviolet absorber composed of a triazine compound (a') represented by the general formula (1'):

[Chemical formula 3]

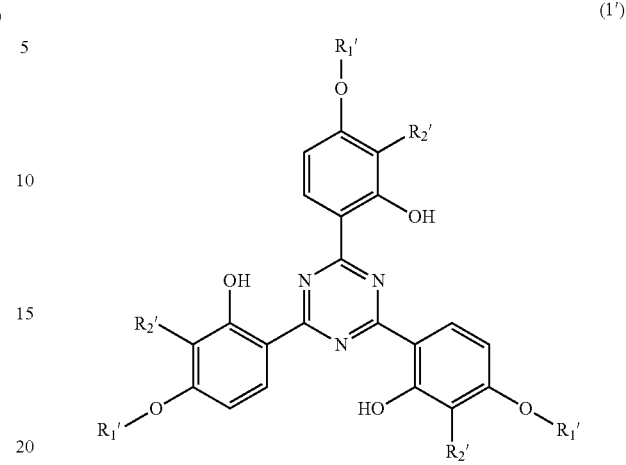

(1')

wherein $R_1'$ represents a linear or branched alkyl group with 4 to 8 carbon atom which is interrupted by an oxygen atom or a carbonyl group, and $R_2'$ represents a methyl group.

Effect of the Invention

According to the present invention, it is possible to provide a sunscreen cosmetic composition which has an excellent effect of the ultraviolet absorber at the short and long wavelength sides. According to the present invention, a sunscreen cosmetic composition containing an emulsified composition containing an ultraviolet absorber that has good long-term storage stability can be provided by emulsifying the ultraviolet absorber using a specific emulsifier.

MODE FOR CARRYING OUT THE INVENTION

Figure 1:
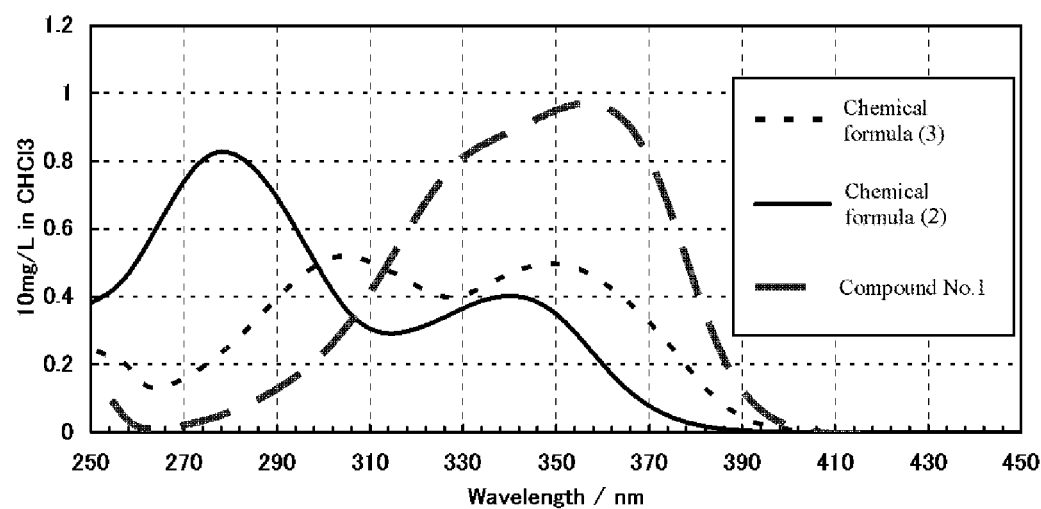
FIG. 1 is a view showing UV spectra of ultraviolet absorbers represented by Compound No. 1 and chemical formulae (2) and (3).

Hereinafter, the sunscreen cosmetic composition of the present invention containing the ultraviolet absorber composed of the triazine compound (a) and the triazine compound (b) will be specifically described based on preferred embodiments. The triazine-based compound to be used as an ultraviolet absorber in the sunscreen cosmetic composition of the present invention will be described below.

The sunscreen cosmetic composition of the present invention contains the ultraviolet absorber composed of the triazine compound (a) represented by the general formula (1) above and the triazine compound (b) represented by chemical formula (2) above.

Examples of the linear or branched alkyl group with 1 to 12 carbon atoms represented by $R_1$ of the general formula (1) above according to the present invention include a linear or branched alkyl group such as methyl, ethyl, propyl, isopropyl, butyl, isobutyl, secondary butyl, tertiary butyl, amyl, isoamyl, tertiary amyl, hexyl, heptyl, n-octyl, isooctyl, tertiary octyl, 2-ethylhexyl, nonyl, isononyl, decyl, undecyl, and dodecyl. Among them, one with 4 to 8 carbon atoms is preferred.

Examples of the cycloalkyl group with 3 to 8 carbon atoms represented by $R_1$ of the general formula (1) above include cyclopropyl, cyclopentyl, cyclohexyl, cycloheptyl, and the like.

Examples of the aryl group with 6 to 18 carbon atoms represented by $R_1$ of the general formula (1) above or the alkyl aryl group with 7 to 18 carbon atoms include phenyl, naphthyl, 2-methylphenyl, 3-methylphenyl, 4-methylphenyl, 4-vinylphenyl, 3-isopropylphenyl, 4-isopropylphenyl, 4-buthylphenyl, 4-isobutylphenyl, 4-tertiary butylphenyl, 4-hexylphenyl, 4-cyclohexyl phenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tertiary butylphenyl, 2,5-di-tertiary butylphenyl, 2,6-di-tertiary butylphenyl, 2,4-di-tertiary pentylphenyl, 2,5-di-tertiary amylphenyl, 2,5-di-tertiary octylphenyl, biphenyl, 2,4,5-trimethyl phenyl, and the like. Examples of the arylalkyl group with 7 to 18 carbon atoms include benzyl, phenethyl, 2-phenylpropane-2-yl, diphenylmethyl, and the like.

Examples of the alkenyl group with 3 to 8 carbon atoms represented by $R_1$ and $R_2$ in the general formula (1) above include linear or branched propenyl, butenyl, pentenyl, hexenyl, heptenyl, and octenyl regardless of the unsaturated bond position.

$R_1$ in the general formula (1) above is preferably a linear or branched alkyl group (particularly linear) with 1 to 12 carbon atoms (particularly 4 to 8) (with the proviso that the alkyl groups may be substituted by a hydroxy group, a halogen atom or an alkoxy group with 1 to 12 carbon atoms or may be interrupted by an oxygen atom, a sulfur atom, a carbonyl group, an ester group, an amide group or an imino group.). When the alkyl group is interrupted by a carbonyl group or an amide group, the carbon atom included in the carbonyl group or the amide group is not included in the number of carbon atoms of the alkyl group.

In the general formula (1) above, examples of the alkyl group with 1 to 8 carbon atoms represented by $R_2$ include methyl, ethyl, propyl, isopropyl, butyl, secondary butyl, tertiary butyl, isobutyl, amyl, tertiary amyl, octyl, tertiary octyl, and the like. Among them, a methyl group is preferred because of excellent ultraviolet absorption capability.

Examples of the triazine-based compound represented by the general formula (1) above include Compound Nos. 1 to 5 below, and the like.

[Chemical formula 4]

Compound No. 1

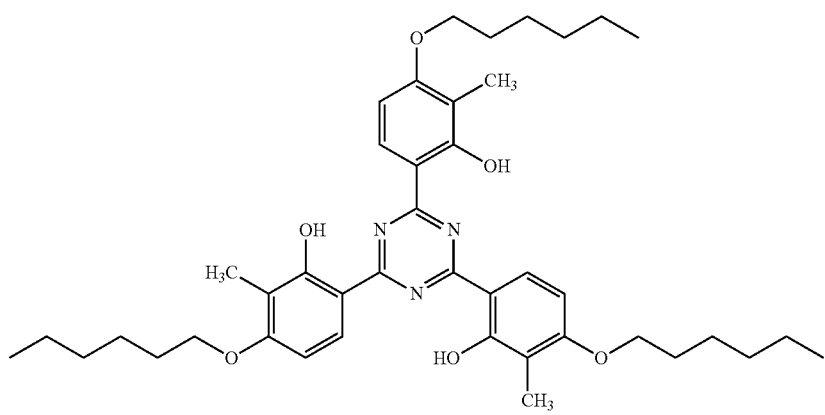

[Chemical formula 5]

Compound No. 2

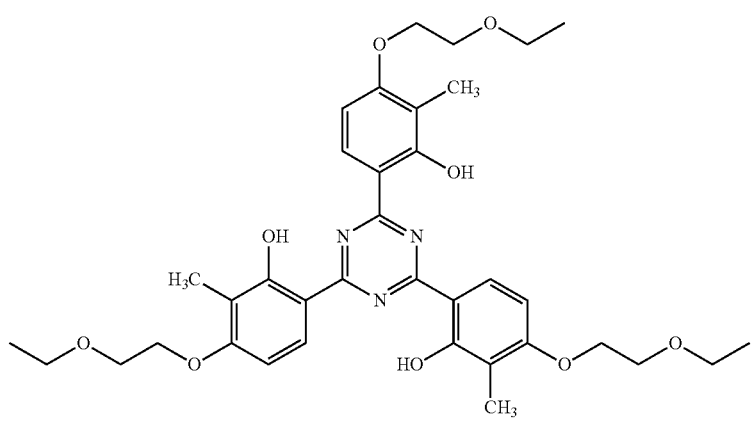

[Chemical formula 6]

Compound No. 3

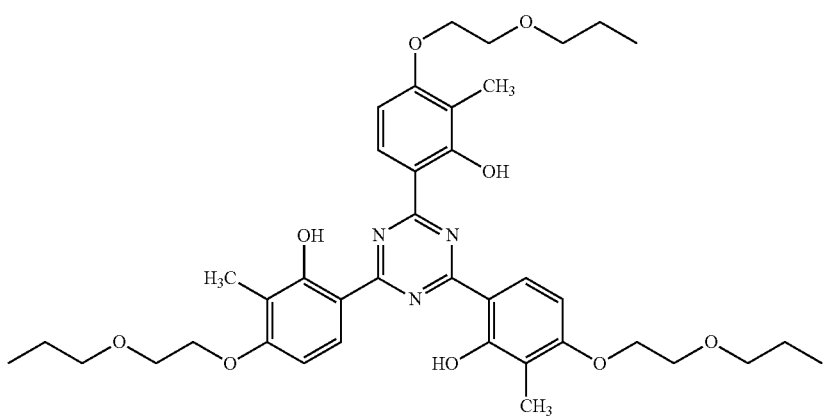

[Chemical formula 7]

Compound No. 4

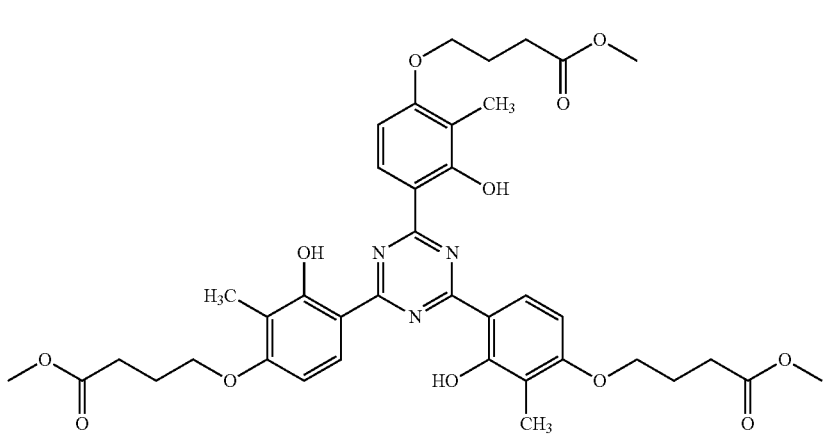

[Chemical formula 8]

Compound No. 5

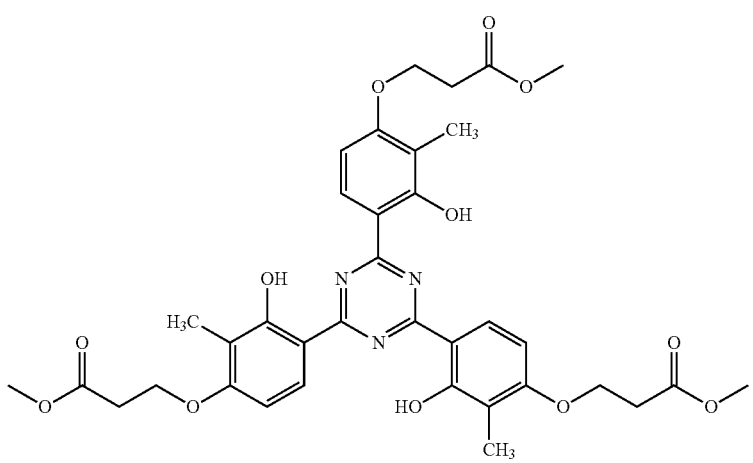

Figure 2:
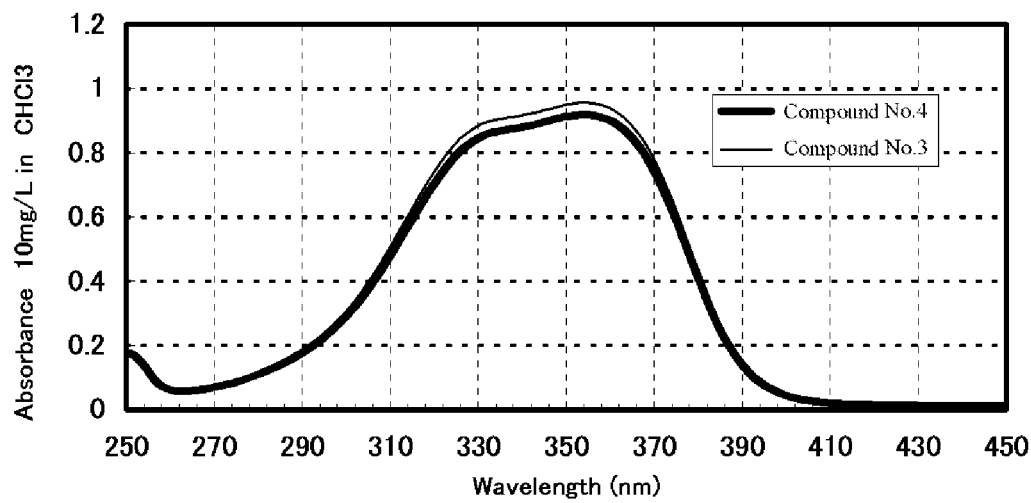
FIG. 2 is a view showing UV spectra of ultraviolet absorbers of Compound Nos. 3 and 4 which can be added alone in the present invention.

A method of synthesizing the triazine compound represented by the general formula (1) above or chemical formula (2) is not particularly limited and the compound can be synthesized by any procedure in a normal organic synthesis. As a purification method, distillation, recrystallization, reprecipitation, a method of using a filter medium/adsorbent, or the like can be suitably used. The UV spectrum of the triazine compound represented by the general formula (1) above or chemical formula (2) is shown in FIGS. 1 and 2. As for the triazine compound represented by the general formula (1) above, as a typical example, the UV spectrum of Compound No. 1 is shown in FIG. 1 and UV spectra of Compound Nos. 3 and 4 are shown in FIG. 2.

The sunscreen cosmetic composition of the present invention may be further blended with the benzotriazol compound represented by chemical formula (3) below if necessary. The compound is referred to as methylene-bis(2-hydroxy-5-tertiary octyl-3-(benzotriazol-2-yl)phenyl, also referred to as 2,2-methylene-bis{4-(1,1,3,3-tetramethylbutyl)-6-(2H-benzotriazol-2-yl)phenol. It is a high-molecular-weight type ultraviolet absorber proposed in JP-A No. 61-118373 and widely used for polycarbonate and the like as an ultraviolet absorber.

The UV spectrum of the benzotriazol compound is shown in FIG. 1.

[Chemical formula 9]

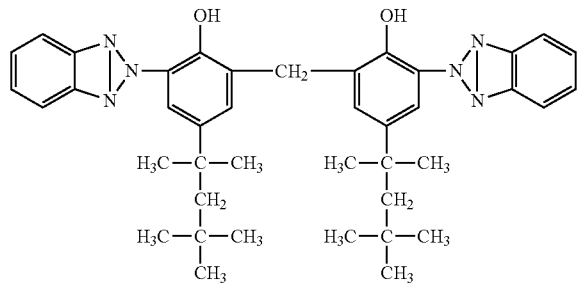

(3)

The blending amount of the triazine compound (a) represented by the general formula (1) above, the triazine compound (b) represented by chemical formula (2) above, and the benzotriazol compound (c) represented by chemical formula (3) above to be added if necessary varies depending on the product form. The total blending amount of the three compounds in the sunscreen cosmetic composition is usually from 0.1 to 20% by mass, more preferably from 0.5 to 10% by mass. When the blending amount is less than 0.1% by mass, it is difficult to sufficiently exert the ultraviolet absorption effect. On the other hand, when the blending amount is 20% by mass or more, improvement in the effect commensurate with an increase of the blending amount is not given and the texture is also impaired, which is not economical.

The content of the triazine compound (a) in the ultraviolet absorber composed of the triazine compound (a) and the triazine compound (b), and further, the benzotriazole compound (c) to be added if necessary is preferably from 10 to 90% by mass, still more preferably from 20 to 80% by mass. The content of the triazine compound (b) in the ultraviolet absorber is preferably from 10 to 90% by mass, still more preferably from 20 to 80% by mass. The content of the benzotriazole compound (c) in the ultraviolet absorber is preferably from 0 to 50% by mass, still more preferably from 5 to 35% by mass.

Since the ultraviolet absorber to be used in the present invention is insoluble, it is usually added to an oily cosmetic base material and mixed so as to be formed into a sunscreen cosmetic composition. The sunscreen cosmetic composition of the present invention can be in any form such as ointment, cream, milky lotion, lotion, cataplasm, spray, and oil solution.

In the present invention, it has been found that an emulsified composition containing an ultraviolet absorber with good long-term storage stability can be provided by adding an emulsifier having a polyether chain reacted with two or more alkylene oxides as a hydrophilic group and a hydrocarbon group with 1 to 30 carbon atoms as a hydrophobic group. The emulsified composition containing an ultraviolet absorber can be used as a raw material preparation to be added to the sunscreen cosmetic composition of the present invention. Further, the emulsified composition containing an ultraviolet absorber itself can be directly used as the sunscreen cosmetic composition of the present invention.

Examples of the emulsifier above having a polyether chain reacted with two or more alkylene oxides as a hydrophilic group and a hydrocarbon group with 1 to 30 carbon atoms as a hydrophobic group include alkyl (or alkenyl) ether of a polyoxyethylene polyoxypropylene block or random copolymer, alkyl (or alkenyl)phenyl ether of a polyoxyethylene polyoxypropylene block or random copolymer, ethers such as polysaccharide, monosaccharide, or oligosaccharide ether of a polyoxyethylene polyoxypropylene block or random copolymer; fatty acid ester of polyoxyethylene polyoxypropylene block or random copolymerization, and esters obtained by estification reaction of the above ethers with fatty acid.

Among these compounds, a particularly preferable compound as the emulsifier above is a compound represented by the general formula (4) below.

$$RO\text{-}(AO)_n\text{-}H \qquad (4)$$

wherein R is a hydrocarbon group with 8 to 30 carbon atoms, A is two or more alkylene groups with 2 to 4 carbon atoms, an ethylene group is more than 50 mol % of the total, and n represents a number of 8 to 80.

In the general formula (4) above, R is a hydrocarbon group with 8 to 30 carbon atoms. Examples of the hydrocarbon group include an alkyl group, an alkenyl group, and an aryl group, and the like. Examples of the alkyl group include octyl, 2-ethylhexyl, secondary octyl, nonyl, secondary nonyl, decyl, secondary decyl, undecyl, secondary undecyl, dodecyl, secondary dodecyl, tetradecyl, secondary tetradecyl, hexadecyl, secondary hexadecyl, stearyl, eicosyl, docosyl, tetracosyl, triacontyl, 2-butyloctyl, 2-butyldecyl, 2-hexyloctyl, 2-hexyldecyl, 2-octyldecyl, 2-hexyldodecyl, 2-octyldodecyl, 2-decyltetradecyl, 2-dodecylhexadecyl, 2-hexadecyloctadecyl, 2-tetradecyloctadecyl, monomethyl-branched-isostearyl, eicosyl, heneicosyl, hexacosyl, heptacocyl, octacosyl, nonacosyl, triacontyl, and the like.

As the alkenyl group, for example, one in which a methylene group of an optional position in the alkyl group is replaced by —CH=CH— is cited.

Examples of the aryl group include xylyl, cumenyl, mesityl, phenethyl, styryl, cinnamyl, benzhydryl, trityl, ethylphenyl, propylphenyl, buthylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl, β-naphthyl groups, and the like.

Among these hydrocarbon groups, the alkyl group or alkenyl group not containing a benzene ring as R is preferred. The number of carbon atoms is preferably from 8 to 24, still more preferably from 8 to 20, most preferably from 8 to 16.

In the general formula (4) above, A is two or more alkylene groups with 2 to 4 carbon atoms. Examples of A include ethylene, propylene, methylethylene, butylene, 1-methylpropylene, 2-methylpropylene, ethylethylene, and the like. These can be derived from ethylene oxide, propylene oxide, butylene oxide, tetrahydrofuran (1,4-butylene oxide) and the like.

When A is two or more alkylene groups, any combination can be used as an emulsifier. In the general formula (4) above, a preferred combination is a combination of an ethylene group derived from ethylene oxide and an alkylene group derived from another alkylene oxide. Another alkylene oxide to combine with the ethylene group is preferably propylene oxide or butylene oxide, most preferably propylene oxide. The polymerization form of alkylene oxide to be added is not limited and it may be random copolymerization of ethylene oxide and one or two or more alkylene oxides, block copolymerization or the like. Among them, the random copolymerization is preferred from the viewpoint of the stability of the emulsified composition containing an ultraviolet absorber.

From the viewpoint of emulsifiability, the percentage of the ethylene group in A is 50 mol % or more, preferably from 55 to 99 mol %, more preferably from 60 to 95 mol %, still more preferably from 68 to 92 mol % based on the total mol. When the percentage of the ethylene group is less than 50 mol %, performance as an emulsifier is not sufficiently exerted and thus an ultraviolet ray inhibitor may not be uniformly emulsified. When the ratio of the ethylene group is 100 mol %, the melting point becomes high, preservation stability may be deteriorated by deposition or the like.

In the general formula (4) above, n represents a number of 8 to 80, preferably a number of 8 to 70, more preferably a number of 8 to 60, still more preferably a number of 8 to 40, most preferably a number of 8 to 30. When n is less than 8, performance as an emulsified composition may not be sufficiently exerted. When n is greater than 80, emulsification stability may be deteriorated.

The emulsified composition containing an ultraviolet absorber is a composition which contains the emulsifier represented the general formula (4) above, water, and an ultraviolet absorber. Here, as the ultraviolet absorber, an ultraviolet absorber which contains the triazine compound (a) represented by the general formula (1) above and the triazine compound (b) represented by chemical formula (2) above, and further contains the benzotriazol compound (c) represented by chemical formula (3) above if necessary is used. Other ultraviolet absorbers and hindered amine-based light stabilizers can be used at a level that does not impair the performance of the sunscreen cosmetic composition.

In the emulsified composition containing an ultraviolet absorber, the triazine compounds (a) and (b) above to be used as an ultraviolet absorber, and further, the benzotriazol compound (c) to be used if necessary are used in a total amount of preferably 1 to 50% by mass, more preferably 10 to 45% by mass, most preferably 15 to 40% by mass.

In the emulsified composition containing an ultraviolet absorber, the amount of the emulsifier is preferably from 1 to 40% by mass, more preferably from 2 to 30% by mass, most preferably from 5 to 20% by mass. An amount of less than 1% by mass may allow sufficient emulsification to be impossible and an amount of more than 40% by mass makes physical properties of the composition worsen, which is not preferred.

In this regard, in order to stably disperse the components constituting the emulsified composition containing an ultraviolet absorber in water to have an average particle diameter of 150 nm or less, the components can be emulsified by using greater than 40% by mass of the emulsifier in the emulsified composition containing an ultraviolet absorber.

In the emulsified composition containing an ultraviolet absorber, the content of water to be used is preferably from 10 to 80% by mass, more preferably from 20 to 70% by mass, most preferably from 30 to 60% by mass.

As for a method of producing the emulsified composition containing an ultraviolet absorber, any known emulsification method can be used without particular restriction. For example, a phase inversion emulsification method, a mechanically forced emulsification method, and the like are cited. Although both methods may be used, the phase inversion emulsification method is preferred in order to obtain an emulsified composition with high storage stability. The phase inversion emulsification method can be performed in accordance with an ordinary manner. As equipment to be used to perform the phase inversion emulsification method, for example, stirring by a high-speed rotating propeller, a homomixer [manufactured by Tokushu Kika Kogyo], a high-pressure homogenizer, an ultrasonic emulsifier, and the like can be used.

The emulsified composition containing an ultraviolet absorber is an O/W type emulsified composition obtained by dispersing an ultraviolet absorber which is an oily component, in water.

When the emulsified composition containing an ultraviolet absorber is used as a raw material preparation to be added to the sunscreen cosmetic composition of the present invention, the additive amount of the emulsified composition containing an ultraviolet absorber to the sunscreen cosmetic composition of the present invention is preferably from 0.1 to 40% by mass, more preferably from 1 to 30% by mass. Further, it is preferable to add the emulsified composition containing an ultraviolet absorber above so that the content of the ultraviolet absorber in the sunscreen cosmetic composition is from 0.1 to 20% by mass.

Other components normally used for a sunscreen cosmetic composition may be arbitrarily added to the sunscreen cosmetic composition of the present invention containing the above ultraviolet absorbers if necessary, unless the effect of the present invention is impaired. Examples thereof include powder components, liquid fat, solid fat, waxes, hydrocarbon oils, higher fatty acids, higher alcohols, esters, silicone oils, anionic surfactants, cationic surfactants, amphoteric surfactants, nonionic surfactants, moisturizers, water-soluble polymers, thickeners, film-forming agents, metal ion sequestrants, lower alcohols, polyhydric alcohols, saccharides, amino acids, organic amines, polymer emulsions, pH adjusters, skin nutrients, vitamins, antioxidants, antioxidant aids, perfumes, water, and the like. Ordinary preparation methods can be used in accordance with desired product forms.

Examples of the powder component include inorganic powder (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate (calcined gypsum), calcium phosphate, fluorine apatite, hydroxyapatite, ceramic powder, metallic soap (for example, zinc myristate, calcium palimitate, and aluminum stearate), boron nitride, and the like); organic powder (for example, polyamide resin powder (nylon powder), polyethylene powder, polymethylmethacrylate powder, polystyrene powder, styrene-acrylic acid copolymer resin powder, benzoguanamine resin powder, poly(tetrafluoroethylene) powder, cellulose powder), and the like; inorganic white pigment (for example, titanium dioxide, zinc oxide, and the like); inorganic red pigment (for example, iron oxide (colcothar), iron titanate, and the like); inorganic brown pigment (for example, γ-iron oxide, and the like); inorganic yellow pigment (for example, yellow iron oxide, loess, and the like); inorganic black pigment (for example, black iron oxide, lower titanium oxide, and the like); inorganic purple pigment (for example, mango violet, cobalt violet, and the like); inorganic green pigment (for example, chrome oxide, chrome hydroxide, cobalt titanate, and the like); inorganic blue pigment (for example, ultramarine, iron blue, and the like); pearl pigment (for example, titanium oxide coated mica, titanium oxide coated bismuth oxychloride, titanium oxide coated talc, colored titanium oxide coated mica, bismuth oxychloride, argentine, and the like); metal powder pigment (for example, aluminum powder, copper powder, and the like); organic pigment such as zirconium, barium, or aluminum lake (for example, organic pigment such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, and the like); natural pigment (for example, chlorophyll, β-carotene, and the like), and the like.

Examples of the liquid fat include avocado oil, camellia oil, turtle oil, macadamia nuts oil, corn oil, mink oil, olive oil, rapeseed oil, egg yolk oil, sesame oil, persic oil, a wheat germ oil, sasanqua oil, castor oil, flaxseed oil, safflower oil, cotton seed oil, perilla oil, soybean oil, arachis oil, tea seed oil, kaya oil, rice bran oil, Chinese tung oil, Japanese tung oil, jojoba oil, germ oil, triglycerol, and the like.

Examples of the solid fat include cacao butter, coconut oil, horse fat, hydrogenated coconut oil, palm oil, beef fat, mutton suet, hydrogenated beef fat, palm kernel oil, lard, beef bones fat, Japan wax kernel oil, hardened oil, neat's-foot fat, Japan wax, hydrogenated caster oil, and the like.

Examples of the waxes can include yellow bees wax, candelilla wax, cotton wax, carnauba wax, bayberry wax, insect wax, spermaceti wax, montan wax, bran wax, lanolin, kapok wax, lanolin acetate, liquid lanolin, sugarcane wax, lanolin fatty acid isopropyl, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, POE hydrogenated lanolin alcohol ether arachis oil.

Examples of the hydrocarbon oil include liquid paraffin, ozokerite, squalane, pristane, paraffin, ceresin, squalene, vaseline, microcrystallin wax, and the like.

Examples of the higher fatty acid include lauric acid, myristic acid, palmitic acid, stearic acid, behenic acid, oleic acid, undecylenic acid, tallic acid, isostearic acid, linoleic acid, linolenic acid, eicosapentaenoic acid (EPA), docosahexaenoic acid (DHA), and the like.

Examples of the higher alcohol include linear alcohols (for example, lauryl alcohol, cetyl alcohol, stearyl alcohol, behenyl alcohol, myristyl alcohol, oleyl alcohol, cetostearyl alcohol, and the like); and branched chain alcohols (for example, monostearylglycerin ether (batyl alcohol), 2-decyltetradecinol, lanolin alcohol, cholesterol, phytosterol, hexyldodecanol, isostearyl alcohol, octyldodecanol, and the like), and the like.

For example, synthetic ester oil can be used as ester.

Examples of the synthetic ester oil include tripropylene glycol di-neo-pentanoate, isononyl isononanoate, isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, di-penta erythritol fatty acid ester, N-alkyl glycol monoiso stearate, neopentyl glycol dicaprate, diisostearyl malate, glycerol di-2-heptyl undecanoate trimethyrol propane tri-2-ethyl hexanoate, trimethyrol propane triisostearate, tetra-2-ethyl hexanoate pentaerythritol, glycerol tri-2-ethyl hexanoate, glycerol trioctanoate, glycerol triisopalmitate, trimethyrol propane triisostearate, cetyl 2-ethylhexanoate, 2-ethylhexyl palmitate, glycerol trimyristate, glyceride tri-2-heptyl undecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-etylhexyl sebacate, 2-hexyldecyl myristate, 2-hexyldecyl palmitate, 2-hexyldecyl adipate, diisopropyl sebacate, 2-ethylhexyl succinate, triethyl citrate, and the like.

Examples of the silicone oil include chain polysiloxanes (for example, dimethylpolysiloxane, methylphenylpolysiloxane, diphenylpolysiloxane); cyclic polysiloxane (for example, octamethylcyclotetrasiloxane, decamethylcyclopentasiloxane, dodecamethylcyclohexasiloxane, and the like), silicone resins having a three dimensional network structure, silicone rubbers, various modified polysiloxanes (for example, amino-modified polysiloxane, polyether-modified polysiloxane, alkyl-modified polysiloxane, fluorine-modified polysiloxane, and the like), and the like.

In the present invention, anionic surfactants, cationic activators, ampholytic surfactants, and non-ionic surfactants can be arbitrary used in addition to the emulsifiers.

Examples of the anionic surfactants include fatty acid soap (for example, sodium laurate, sodium palmitate, and the like); higher alkyl sulfate ester salt (for example, sodium lauryl sulfate, potassium lauryl sulfate, and the like); alkyl ether sulfate ester salt (for example, POE-lauryl sulfate triethanolamine, sodium POE-lauryl sulfate, and the like); N-acyl sarcosinic acid (for example, sodium lauroyl sarcocinate, and the like); higher fatty acid amide sulfonate (for example, sodium N-myristoyl-N-methyl taurine, sodium coconut oil fatty acid methyl tauride, sodium laurylmethyl tauride, and the like); phosphate ester salt (sodium POE-oleylether phosphate, POE-stearylether phosphate, and the like); sulfosuccinate (for example, sodium di-2-ethylhexyl sulfosuccinate, sodium monolauroyl monoethanolamide polyoxyethylene sulfosuccinate, sodium lauryl polypropylene glycol sulfosuccinate, and the like); alkylbenzene sulfonate (for example, sodium linear dodecylbenzene sulfonate, triethanolamine linear dodeylbenzene sulfonate, linear dodecylbenzene sulfonate, and the like); higher fatty acid ester sulfate ester salt (for example, sodium hydrogenated coconut oil fatty acid glycerin sulfate, and the like), N-acyl glutamate (for example, monosodium N-lauroyl glutamate, disodium N-stearoyl glutamate, monosodium N-myristoyl-L-glutamate, and the like); sulfonated oil (for example, Turkey red oil, and the like); POE-alkyl ether carboxylic acid; POE-alkyl aryl ether carboxylate; α-olefine sulfonate; higher fatty acid ester sulfonate, secondary alcohol sulfate ester salt, higher fatty acid alkylolamide sulfate ester salt, sodium lauroyl monoethanolamide succinate; N-palmitoyl asparaginate ditriethanolamine; sodium casein, and the like.

Examples of the cationic surfactants include alkyltrimethyl ammonium salt (for example, stearyltrimethyl ammonium chloride, lauryltrimethyl ammonium chloride, and the like); alkylpyridinium salt (for example, cetylpyridinium chloride, and the like); distearyldimethyl ammonium chloride dialkyldimethyl ammonium salt; poly (N,N'-dimethyl-3,5-methylenepiperidinium) chloride; alkyl quaternary ammonium salt; alkyldimethylbenzyl ammonium salt; alkylisoquinolinium salt; dialkylmorphonium salt; POE alkylamine; alkylamine salt; polyamine fatty acid derivative; amyl alcohol fatty acid derivative; benzalkonium chloride; benzethonium chloride, and the like.

Examples of the ampholytic surfactants include imidazoline base ampholytic surfactants (for example, sodium 2-undecyl-N,N,N-(hydroxyethylcarboxymethyl)-2-imidazoline, 2-cocoyl-2-imidazolinium hydroxide-1-carboxyethyloxy)-2-sodium salt, and the like); betaine base surfactants (for example, 2-heptadecyl-N-carboxymethyl-N-hydroxyethyl-imidazolinium betaine, lauryldimethyl aminoacetate betaine, alkyl betaine, amidobetaine, sulfobetaine, and the like), and the like.

Examples of the non-ionic surfactants include lipophilic non-ionic surfactants and hydrophilic non-ionic surfactants. Examples of the lipophilic non-ionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate, and the like); glyceryl polyglyceryl fatty acids (for example, glyceryl monocotton oil fatty acid, glyceryl monoerucate, glyceryl sesquioleate, glyceryl monostearate, glyceryl α,α'-oleate pyroglutamate, glyceryl monostearate malate, and the like); propylene glycol fatty acid esters (for example, propylene glycol monostearate, and the like); hydrogenated caster oil derivative; glyceryl alkyl ether, and the like.

Examples of the hydrophilic non-ionic surfactant include POE-sorbitan fatty acid esters (for example, POE-sorbitan monooleate, POE-sorbitan monostearate, POE sorbitan monooleate, POE-sorbitan tetraoleate, and the like); POE-sorbit fatty acid esters (for example, POE-sorbit monolaurate, POE-sorbit monooleate, POE-sorbit pentaoleate, POE-sorbit monostearate, and the like), POE-glyceryl fatty acid esters (for example, POE-monooleate such as POE-glyceryl monostearate, POE-glyceryl monoisostearate, and POE-glyceryl triisostearate, and the like); POE-fatty acid esters (for example, POE-distearate, POE-monodioleate, ethyleneglycol distearate, and the like); POE-alkyl ethers (for example, POE-lauryl ether, POE-oleyl ether, POE-stearyl ether, POE-behenyl ether, POE-2-octyldodecyl ether, POE-cholestanol ether, and the like); puluronic types (for example, Puluronic, and the like), POE•POP-alkyl ethers (for example, POE •POP-cetyl ether, POE •POP-2-decyltetradecyl ether, POE •POP-monobutyl ether, POE•POP-hydrogenated lanoline, POE•POP-glycerin ether, and the like); tetra POE•tetra POP-ethylenediamine condensation products (for example, Tetronic, and the like); POE-castor oil hydrogenated castor oil derivatives (for example, POE-caster oil, POE-hydrogenated caster oil, POE-hydrogenated caster oil monoisostearate, POE-hydrogenated castor oil triisostearate, POE-hydrogenated caster oil monopyroglutamate monoisostearate diester, POE-hydrogenated oil maleate, and the like); POE-beeswax/lanoline derivatives (for example, POE-sorbitol beeswax, and the like); alkanolamide (for example, coconut oil fatty acid diethanolamide, lauric acid monoethanolamide, fatty acid isopropanolamide, and the like); POE-propyleneglycol fatty acid ester; POE-alkyl amine; POE-fatty acid amide; sucrose fatty acid ester; alkylethoxydimethylamine oxide; trioleyl phosphoric acid, and the like.

Examples of the moisturizers include polyethylene glycol, propylene glycol, glycerin, 1,3-butylene glycol, xylitol, sorbitol, maltitol, chondroitin sulfate, hyaluronic acid, mucoitinsulfuric acid, caronic acid, atelocollagen, cholesteryl-12-hydroxystearate, sodium lactate, bile salt, dl-pyrrolidonecarboxylic-acid salt, short-chain soluble collagen, diglycerin (EO)PO adduct, *Rosa roxburghii* extract, *Achillea milefolium* extract, melilot extract, and the like.

Examples of the water-soluble polymer include natural, semi-synthetic, and synthetic water-soluble polymers. Examples of the natural water-soluble polymer include plant-based polymer (for example, Arabia gum, tragacanth gum, galactan, guar gum, carob gum, karaya gum, carrageenan, pectin, agar, quince seed (*Cyclonia oblonga*), algae colloid (brown algae extract), starch (rice, corn, potato, wheat), glicyrrhizic acid), microorganisms based polymer (for example, xanthan gum, dextran, succinoglycan, pullulan, and the like), and animal-based polymer (for example, collagen, casein, albumin, gelatine, and the like), and the like.

Examples of the semi-synthetic water-soluble polymers include starch-based polymer (for example, carboxymethyl starch, methylhydroxypropyl starch, and the like), cellulose-based polymer (methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, crystalline cellulose, cellulose powder, and the like), and algin acid-based polymer, (for example, alginate sodium, propylene glycol ester alginate, and the like), and the like.

Examples of the synthetic water-soluble polymers include vinyl-based polymer (for example, polyvinyl alcohol, polyvinyl methyl ether, polyvinylpyrrolidone, carboxyvinylpolymer, and the like); polyoxyethylene-based polymer (for example, polyoxyethylenepolyoxypropylene copolymer of polyethylene glycol 20,000, 40,000 and 60,000, and the like); acrylic-based polymer (for example, sodium polyacrylate, polyethylacrylate, polyacrylamide, and the like); polyethyleneimine; cationic polymer, and the like.

Examples of the thickeners include Arabia gum, carrageenan, karaya gum, tragacanth gum, carob gum, quince seed, (*cyclonia oblonga*), casein, dextrin, gelatin, sodium pectate, alginate sodium, methylcellulose, ethylcellulose, CMC, hydroxyethylcellulose, hydroxypropylcellulose, PVA, PVM, PVP, sodium polyacrylate, carboxyvinylpolymer, locust bean gum, guar gum, tamarind gum, dialkyldimethylammonium cellulose sulfate, xanthan gum, aluminium magnesium silicate, bentonite, hectorite, magnesium aluminium silicate (veegum), laponite, silicic anhydride, and the like.

Examples of the sequestrant include 1-hydroxyethane-1, 1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, sodium ethylenediaminehydroxyethyl triacetate, and the like.

Examples of the lower alcohol include ethanol, propanol, isopropanol, isobutyl alcohol, t-butyl alcohol, and the like.

Examples of the polyhydric alcohol include dihydric alcohol (for example, ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, and the like); trihydric alcohol (for example, glycerin, trimethylolpropane, and the like); tetrahydric alcohol (for example, pentaerythritol such as 1,2,6-hexanetriol, and the like); pentahydric alcohol (for example, xylitol, and the like); hexahydric alcohol (for example, sorbitol, mannitol, and the like); polyhydric alcohol polymer (for example, diethylene glycol, dipropylene glycol, triethylene glycol, polypropylene glycol, tetraethylene glycol, diglycerin, polyethylene glycol, triglycerin, tetraglycerin, polyglycerin, and the like); dihydric alcohol alkyl ethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, and the like); dihydric alcohol alkyl ethers (for example, diethylene glycol monomethyl ether, diethylene glycol monoethyl ether, diethylene glycol monombutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, and the like); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, and the like); glycerin monoalkyl ether (for example, chimyl alcohol, selachyl alcohol, batyl alcohol, and the like); sugar alcohol (for example, sorbitol, maltitol, maltotriose, mannitol, sucrose, erythritol, glucose, fructose, starch-degraded sugar, maltose, xylitose, starch-degraded sugar-reduced alcohol, and the like); glysolid, tetrahydrofurfuryl alcohol; POE-tetrahydrofurfuryl alcohol; POP-bytyl ether; POP •POE-butyl ether; tripolyoxypropylene glycerin ether; POP-glycerin ether; POP-glycerin ether phosphoric acid; POP•POE-pentaerythritol ether; polyglycerin, and the like.

Examples of the sugar include monosaccharide, oligosaccharide, and polysaccharide. Examples of the monosaccharide include triose (for example, D-glyceryl aldehyde, dihydroxyacetone, and the like); tetrose (for example, D-erythrose, D-erythrulose, D-threose, erythritol, and the like); pentaose (for example, L-arabinose, D-xylose, L-lyxose, D-arabinose, D-ribose, D-ribulose, D-xylulose, L-xylulose, and the like); hexylose (for example, D-glucose, D-talose, D-psicose, D-galactose, D-fructose, L-galactose, L-mannose, D-tagatose, and the like); heptose (for example, aldoheptose, heplose, and the like); octose (for example, octulose, and the like); deoxy sugar (for example, 2-deoxy-D-ribose, 6-deoxy-L-galactose, 6-deoxy-L-mannose, and the like); amino sugar (for example, D-glucosamine, D-galactosamine, sialic acid, amino uronic acid, muramic acid, and the like); uronic acid (for example, D-grucuronic acid, D-mannuronic acid, L-guluronic acid, D-garacturonic acid, L-iduronic acid, and the like), and the like.

Examples of the oligosaccharide include sucrose, gentianose, umbelliferose, lactose, planteose, isolychnoses, α,α-trehalose, raffinose, lychnoses, umbilicin, stachyose and verbascoses, and the like.

Examples of the polysaccharide include cellulose, quince seed, chondroitin sulfate, starch, galactan, dermatan sulfate, glycogen, Arabia gum, heparan sulfate, hyaluronic acid, tragacanth gum, keratan sulfate, chondroitin, xanthan gum, mucoitinsulfuric acid, guar gum, dextran, keratosulfate, locust bean gum, succinoglycan, and caronic acid, and the like.

Examples of the amino acid include neutral amino acids (for example, threonine, cysteine, and the like), basic amino acids (for example, hydroxylysine, and the like), and the like. Examples of amino acid derivatives include sodium acyl sarcosine (sodium lauroyl sarcosine), acyl glutamate, sodium acyl β-alanine, glutathione, pyrrolidone carboxylate, and the like.

Examples of the orgasmic amine include monoethanolamine, diethanolamine, triethanolamine, morpholine, tri-isopropanolamine, 2-amino-2-methyl-1,3-propanediol, 2-amino-2-methyl-1-propanol, and the like.

Examples of the polymer emulsion include acrylic resin emulsion, ethyl polyacrylate emulsion, acrylic resin liquid, polyacrylic alkyl ester emulsion, polyvinyl acetate resin emulsion, natural rubber latex, and the like.

Examples of the vitamins include vitamins A, B1, B2, B6, C, and E and the derivatives thereof, pantothenic acid and the derivatives thereof, biotin, and the like.

Examples of the antioxidants include tocopherols, dibutylhydroxytoluene, burylhydroxyanisole, gallic acid esters, and the like.

Examples of the antioxidant aid include phosphoric acid, citric acid, ascorbic acid, maleic acid, malonic acid, succinic acid, fumaric acid, kephalin, hexametaphosphate, phytic acid, ethylenediaminetetraacetate, and the like.

Examples of other containable compositions include antiseptic agent (ethylparaben, butylparaben, and the like); antiphlogistic (for example, glycyrrhizic acid derivatives, glycyrrhetic acid derivatives, salicylic acid derivatives, hinokitiol, zinc oxide, allantoin, and the like), lightening agent (for example, placental extract, saxifrage extract, arbutin, and the like); various extract (for example, cork tree bark, Japanese coptis, lithospermum, peony, swertia herb, birch, sage, loquat, carrot, aloe, mallow, iris, grape, mugwort, sponge gourd, lily, saffron, cnidium rhizome, ginger, hypericum, restharrow, garlic, red pepper, citrus unshiu, Japanese angelica, seaweed, and the like); activator (for example, royal jelly, photosenstizer, cholesterol derivatives, and the like); blood circulation promotion agent (for example, nonyl acid vanillyl amide, nicotine acid benzyl ester, nicotine acid β-butoxyethyl ester, capsaicin, zingerone, cantharides tincture, ichthammol, tannic acid, α-borneol, tocopheryl nicotinate, inositol hexanicotinate, cyclandelate, cinnarizine, tolazoline, acetylcholine, verapamil, cepharanthine, γ-oryzanol, and the like); antiseborrheic agent (for example, sulfur, thianthol, and the like), and anti-inflammatory agent (for example, tranexamic acid, thiotaurine, hypotaurine, and the like), and the like.

Further, as an ultraviolet absorber, a water-soluble or oil-soluble ultraviolet absorber can be optionally added to the sunscreen cosmetic composition of the present invention in a range that does not impair the effect of the present invention, in addition to the compounds (a), (b) and (c) above. When an optional ultraviolet absorber is used, the amount is preferably 5 parts by mass or less based on a total amount of 100 parts by mass of the compounds (a), (b), and (c).

Examples of the ultraviolet absorber include other triazine-based ultraviolet absorbers (for example, bisresorcinyl triazine, 2,4-bis{[4-(2-ethylhexyloxy)-2-hydroxy]phenyl}-6-(4-methoxyphenyl)1,3,5-triazine, octyltriazon(2,4,6-tris{4-(2-ethylhexyloxycarbonyl)anilino}1,3,5-triazine), and the like); benzoic acid-based ultraviolet absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, and the like); anthranilic acid-based ultraviolet absorbers (for example, homomethyl-N-acetylanthranilate, and the like); salicylic acid-based ultraviolet absorbers (for example, amyl salicylate, menthyl salicylate, homomethyl salicylate, octyl salicylate, phenyl salicylate, benzyl salicylate, p-isopropanolphenyl salicylate, and the like); cinnamic acid-based ultraviolet absorbers (for example, octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, diethanolamine ethoxy cinnamate, and the like); benzophenone-based ultraviolet absorbers (for example, (2-[4-(diethylamino)-2-hydroxybenzoyl]benzoic acid hexyl ester, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, and the like); 3-(4'-methylbenzylidene)-d,l-camphor, 3-benzylidene-d,l-camphor; 2-phenyl-5-methylbenzoxazol; 2,2'-hydroxy-5-methylphenylbenzotriazol, 2-(2'-hydroxy-5'-t-octylphenyl)benzotriazol, 2-(2'-hydroxy-5'-methylphenylbenzotriazol; dibenzalazine; dianisoylmethane; 5-(3,3-dimethyl-2-norbornylidene)-3-pentane-2-one; phenyl acrylate-based ultraviolet absorbers (for example, 2-ethylhexyl-2-cyano-3,3-diphenyl acrylate, 2-ethyl-2-cyano-3,3-diphenyl acrylate, and the like); phenyl benzimidazole derivatives (for example, phenylbenzimidazole sulfonic acid, disodium phenyl dibenzimidazole tetra sulfonate, and the like); camphor derivatives (for example, 4-methylbenzyliene camphor, terephthalylidene dicamphor sulfonic acid, and the like); phenylbenzo triazole derivatives (for example, hydroxy-(ethylhexyl)phenoxybenzotriazol, methylene bis-benzotriazoryl tetramethylbutylphenol, and the like); and benzal malonate derivatives (for example, dimethicone benzalmalonate, and the like).

In addition to the ultraviolet absorbers, it is preferable that the sunscreen cosmetic composition of the present invention further contains one or more of cinnamic acid derivatives, anthranilate derivatives, salicylic acid derivatives, camphor derivatives, benzalmalonate derivatives, benzimidazole derivatives, p-aminobenzoic acid derivatives, methylenebis(hydroxyphenyl)benzotriazole derivatives, and triazine derivatives. Particularly preferable examples thereof include ethylhexyl salicylate, homosalate, paramethoxy cinnamic acid-2-ethylhexyl(paramethoxy silicic acid-2-ethylhexyl), octocrylene, phenylbenzimidazole sulfonic acid, 4-methylbenzyliene camphor, methylene bis-benzotriazoryl tetramethylbutylphenol, phenylbenzo triazole, diethylamino-hydroxybenzoyl benzoic acid hexylester, hydroxy-(ethylhexyl)phenoxybenzotriazol, bis-ethylhexyl phenol methoxypheny triazine, dimethicone diethyl benzalmalonate, disodium phenyl dibenzimidazole tetra sulfonate, and the like.

A method of producing the sunscreen cosmetic composition of the present invention is not particularly limited. In addition to the method of producing the composition through the emulsified composition containing an ultraviolet absorber, for example, an emulsification method containing adding to one obtained by dispersing an ultraviolet absorber in an aqueous phase or an oil phase in advance by a bead mill and the like, and adding other cosmetic base materials and aids if necessary.

In the sunscreen cosmetic composition of the present invention, as a solvent for solubilization to solubilize an oily component; oil, wax, and generally all oils, lower monohydric alcohols, or polyhydric alcohols can be used. Particularly preferable examples of the monohydric alcohol or polyhydric alcohol include ethanol, isopropanol, propylene glycol, hexylene glycol, glycerin, and sorbitol.

One embodiment of the present invention is an emulsion in a protection cream or milky lotion form which contains fatty alcohol, fatty acid ester (particularly fatty acid triglyceride), lanolin, a natural or synthetic oil or wax, and an emulsifier in the presence of water, in addition to the ultraviolet absorber composed of the triazine compound (a) represented by the general formula (1) above and the triazine compound (b) represented by Chemical formula (2) above.

Another embodiment is constituted of an oily lotion which contains a natural or synthetic oil or wax, lanolin and fatty acid ester, particularly fatty acid glyceride as main components or an oil-alcoholic lotion which contains lower alcohol (for example, ethanol) or glycol (for example, propylene glycol) and/or polyhydric alcohol (for example, glycerin), oil, wax, and fatty acid ester (for example, fatty acid triglyceride) as main components.

The cosmetic composition of the present invention may be one or more lower alcohols or polyhydric alcohols, such as ethanol, propylene glycol, glycerin, and an alcoholic gel containing a thickener (for example, silica). An oil-alcoholic gel further includes a natural or synthetic oil or wax.

Examples of the form of the sunscreen cosmetic composition of the present invention to be obtained in the above manner include liquid form, milky lotion form, cream from, solid powder form, and the like. Examples of the product form of sunscreen cosmetic materials include basic cosmetics such as essence having a sunscreen effect, cosmetic water, milky lotion, cream, pack, makeup base, styling spritz, and shaving lotion; makeup cosmetics such as foundation, face powder, rouge, concealer, eye shadow, eyeliner, eyebrow, and lipstick, and the like.

The sunscreen cosmetic composition of the present invention contains the ultraviolet absorber having a specific structure according to the present invention so that various types of skin damage conditions caused by being exposed to sunlight, such as flush, erythema, and edema and blister formation can be reduced. The sunscreen cosmetic composition of the present invention can simultaneously respond to sunburn in low wavelength and sunburn in high wavelength so that it can exert excellent performance as compared with conventional sunscreen inhibitors.

Titanium oxide itself, which has been conventionally used as a UV-A absorbent, is a white pigment and its opaqueness is disadvantageous. When the ultraviolet absorber according to the present invention is added to the cosmetic composition, there is no problem in the transparency and the blending amount can be increased compared with the case of titanium oxide. Thus, larger optical absorption and light shield effect can be expected.

The sunscreen cosmetic composition of the present invention has an effect for protecting the skin from, particularly UV-A and UV-C wavelengths in combination of the triazine compound (a) represented by the general formula (1) above and the triazine compound (b) represented by chemical formula (2) above, and exhibits higher effect for protecting the skin from the UV-B wavelength in further combination of the benzotriazol compound (c) represented by chemical formula (3).

Further, the ultraviolet absorber in the sunscreen cosmetic composition of the present invention is excellent such that the ultraviolet absorber has a higher compatibility with the oily cosmetic base material due to the use of emulsifiers, thus the blending amount can be freely selected, and the protective effect can be dramatically improved as compared with conventional products while ensuring transparency.

Since the sunscreen cosmetic composition of the present invention described above contains the triazine compound (a) and the triazine compound (b), it has an effect for protecting the skin from UV-A, UV-B, and UV-C wavelengths. Even if the cosmetic composition independently contains the compound represented by the general formula (1') above (particularly, Compound No. 2, Compound No. 3, Compound No. 4 and Compound No. 5) among the triazine-based compounds (a), it can exhibit excellent sunscreen properties. Particularly, Compound No. 4 can be preferably used as the sunscreen cosmetic composition by independently adding it. When the compounds represented by the general formula (1') above are independently added, the explanation described in the sunscreen cosmetic composition of the present invention which contains the triazine compound (a) and the triazine compound (b) can be arbitrary applied to the case.

EXAMPLES

The present invention will be described in detail with reference to Examples. However, the present invention is not limited to the following Examples.

Example 1 and Comparative Example 1

Sunscreen Cream

| Ultraviolet absorber (Compound No. 1) | 3.0 g |
| Ultraviolet absorber (Chemical formula (2)) | 3.0 g |
| 2-ethylhexyl palmitate | 18.0 g |
| Isopropyl-myristate | 44.0 g |
| Polyoxyethylene (20) sorbitan monoorate | 2.0 g |
| Sorbitan monoorate | 2.0 g |
| Propylene glycol | 5.0 g |
| triglyceride 2-ethylhexanoate | 2.0 g |
| Squalane | 6.0 g |
| BHT | 2.0 g |

The above components are mixed and heated to be kneaded at about 50° C. Further, the above components not containing the ultraviolet absorbers are prepared as Comparative example.

Example 2

Sunscreen Cream

A sunscreen cream was prepared in the same manner as Example 1 except that the total blending amount (6.0 g) of the ultraviolet absorber (Compound No. 1) and the ultraviolet absorber (Chemical formula (2)) described in Example 1 was replaced with 6.0 g of the ultraviolet absorber (Compound No. 4).

Example 3

Creamy Foundation

| Ultraviolet absorber (Compound No. 1) | 3.0 g |
| Ultraviolet absorber (Chemical formula (2)) | 3.0 g |

-continued

| Ultraviolet absorber (Chemical formula (3)) | 3.0 g |
| Stearic acid | 5.0 g |
| Glyceryl monostearate | 2.5 g |
| Cetostearyl alcohol | 1.0 g |
| Propylene glycol monolaurate | 3.0 g |
| Squalane | 6.0 g |
| Olive oil | 13.0 g |
| Triethanolamine | 1.5 g |
| Sorbitol | 4.0 g |
| Titanium oxide | 1.0 g |
| Talc | 4.0 g |
| sorbitan polyoxyethylene monostearate | 3.0 g |
| Purified water | 47.0 g |
| (Total: 100.0 g) | |

Ground products of the raw material powder products are used and these are mixed. The resultant mixture is added to an oily raw material, which is stirred and heated at 70° C., followed by addition of water to prepare an emulsified product.

Example 4

Cream

| Ultraviolet absorber (Compound No. 1) | 2.5 g |
| Ultraviolet absorber (Chemical formula (2)) | 2.0 g |
| Sorbitan polyoxyethylene monostearate (60E.O) | 1.0 g |
| Polyoxyethylene sorbitol tetraoleate (60E.O) | 1.5 g |
| Glyceryl monostearate | 1.5 g |
| White beeswax | 2.0 g |
| Paraffin | 2.0 g |
| Stearic acid | 3.0 g |
| Behenyl alcohol | 3.0 g |
| Almond oil | 12.0 g |
| Vitamin E | 0.04 g |
| Silicone oil | 0.1 g |
| Ethyl p-oxybenzoate | 0.2 g |
| Liquid paraffin | 5.0 g |
| 1,3-butylene glycol | 5.0 g |
| Citric acid | 0.3 g |
| Sodium dl-lauroyl-L-glutamate | 0.5 g |
| β-cyclodextrin | 8.0 g |
| Kojic acid | 2.0 g |
| Purified water | 48.36 g |
| (Total: 100.0 g) | |

The above compounds are mixed, stirred, and dissolved to prepare an emulsifier with purified water. The resultant emulsifier is cooled to adjust the pH of the cream to 5.

Example 5

Cosmetic Water

| Ultraviolet absorber (Compound No. 1) | 1.0 g |
| Ultraviolet absorber (Chemical formula (2)) | 1.5 g |
| Polyoxyethylene hydrogenated castor oil (60E.O) | 1.0 g |
| Ethanol | 15.0 g |
| Ethyl p-oxybenzoate | 0.1 g |
| Citric acid | 0.1 g |
| Sodium citrate | 0.3 g |
| Sodium N-lauroyl-L-glutamate | 0.5 g |
| 1,3-butylene glycol | 4.0 g |
| Disodium ethylenediaminetetraacetate | 0.01 g |
| Kojic acid | 2.0 g |

-continued

| | |
|---|---|
| β-cyclodextrin | 1.0 g |
| BHT | 0.5 g |
| Purified water | 74.5 g |
| (Total: 100.0 g) | |

The above composition is uniformly stirred and dissolved to prepare cosmetic water.

Example 6

Lotion

| | |
|---|---|
| Ultraviolet absorber (Compound No. 1) | 3.0 g |
| Ultraviolet absorber (Chemical formula (2)) | 1.0 g |
| Isopropanol | 8.0 g |
| Triethanolamine | 0.5 g |
| Mineral oil | 27.0 g |
| Lanolin oil | 2.0 g |
| Propylene glycol | 3.0 g |
| Cetyl alcohol | 1.0 g |
| Stearic acid | 2.0 g |
| BHT | 1.0 g |
| P-hydroxybenzoate | 1.0 g |
| Perfume | 0.5 g |
| Purified water | 50.0 g |
| (Total: 100.0 g) | |

The above components are heated at about 60° C., an aqueous component and an oily component are dissolved in purified water and oil, respectively. An oil-dissolved substance was gradually added to a water-dissolved substance while sufficiently stirring, which was cooled and perfume was added thereto.

20 mg of the cosmetic compositions of Examples 1 to 6 and Comparative example 1 was applied to an area of 2.5 cm×2.5 cm of the inside of subject's arm and the area was exposed to sunlight for 3 hours, mainly at noon on a clear day. When the cosmetic compositions of Examples 1 to 6 were applied, flush and erythema were not particularly observed and thus these cosmetic compositions were useful as sunscreen cosmetic compositions. On the other hand, in the case of Comparative example 1 to which the ultraviolet absorber was not added, flush and erythema were observed in the skin.

Example 7

Method of Producing Emulsified Composition Containing Ultraviolet Absorber

Ultraviolet absorbers and emulsifiers were placed in a 1000-ml vessel having a homomixer and a temperature rising device and the temperature was increased to 60 to 70° C. while mixing by the homomixer. A certain amount of water was gradually charged into the vessel while observing the condition in the vessel. When a specific amount of water was charged thereto, a phase inversion from W/O emulsion to O/W emulsion was caused. After confirming that, the temperature was cooled to 30 to 40° C. and all the remaining water was added. Thereafter, the mixture was continued to stir for 2 hours and an emulsified composition containing an ultraviolet absorber was obtained.

The type and amount of the ultraviolet absorbers and emulsifiers and the amount of water are shown in [Table 1].

<Storage Stability Test>

80 ml of the emulsified composition containing an ultraviolet absorber thus obtained was placed in a 100-ml closed glass vessel and stored in a thermostat at 50° C. for 30 days. The appearance of the emulsified composition after 10, 20, and 30 days was observed. The results were shown in [Table 2]. In [Table 2], a mark ⊚ indicates uniformity, a mark ○ indicates that the surface is slightly separated, a mark Δ indicates that the surface separation is clearly observed, a mark x indicates that overall non-uniformity or large separation is observed, and a mark xx indicates complete separation.

TABLE 1

| | Example 7 | | | | | | | | | | |
|---|---|---|---|---|---|---|---|---|---|---|---|
| | 1 | 2 | 3 | 4 | 5 | 6 | 7 | 8 | 9 | 10 | 11 |
| A1 | 15 | 15 | 15 | 15 | | | | | | | |
| A2 | | | | | 15 | | | | | | |
| A3 | | | | | | 15 | | | | | |
| A4 | | | | | | | 15 | | | | |
| A5 | | | | | | | | 15 | | | |
| A6 | | | | | | | | | 15 | | |
| A7 | | | | | | | | | | 15 | |
| A8 | | | | | | | | | | | 15 |
| C1 | 10 | 15 | 20 | 10 | 15 | 15 | 15 | 15 | 15 | 15 | 15 |
| C2 | 20 | 15 | 10 | 10 | 15 | 15 | 15 | 15 | 15 | 15 | 15 |
| C3 | | | 10 | | | | | | | | |
| Water | 55 | 55 | 55 | 55 | 55 | 55 | 55 | 55 | 55 | 55 | 55 |

<Emulsifier>
A1: Tridecanol 12EO/3PO random copolymerization product
A2: Tridecanol 25EO/3PO random copolymerization product
A3: Tridecanol 50EO/5PO random copolymerization product
A4: Lauryl alcohol 15EO/3PO random copolymerization product
A5: Lauryl alcohol 8EO/3PO random copolymerization product
A6: Oleyl alcohol 20EO/4PO random copolymerization product
A7: 2-ethylhexyl acid 15EO/3PO random copolymerization product
A8: Butanol 6EO/2PO random copolymerization product
<Ultraviolet absorber>
C1: Compound No. 1
C2: Chemical formula (2)
C3: Chemical formula (3)

TABLE 2

| | | Storage stability test results | | |
|---|---|---|---|---|
| | | After 10 days | After 20 days | After 30 days |
| Example 7 | 1 | ⊚ | ⊚ | ⊚ |
| | 2 | ⊚ | ⊚ | ⊚ |
| | 3 | ⊚ | ⊚ | ⊚ |
| | 4 | ⊚ | ⊚ | ⊚ |
| | 5 | ⊚ | ⊚ | ⊚ |
| | 6 | ⊚ | ⊚ | ⊚ |
| | 7 | ⊚ | ⊚ | ⊚ |
| | 8 | ⊚ | ⊚ | ⊚ |
| | 9 | ⊚ | ⊚ | ⊚ |
| | 10 | ⊚ | ⊚ | ⊚ |
| | 11 | ⊚ | ⊚ | ⊚ |

The invention claimed is:
1. A sunscreen cosmetic composition, comprising:
an oily component, said oily component being propylene glycol; and
an ultraviolet absorber composed of a triazine compound (a) represented by the general formula (1) below and a triazine compound (b) represented by chemical formula (2) below,

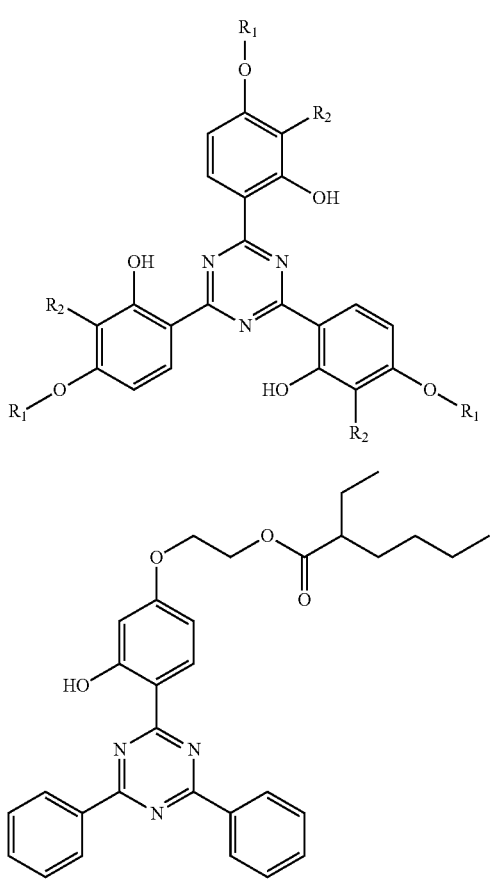

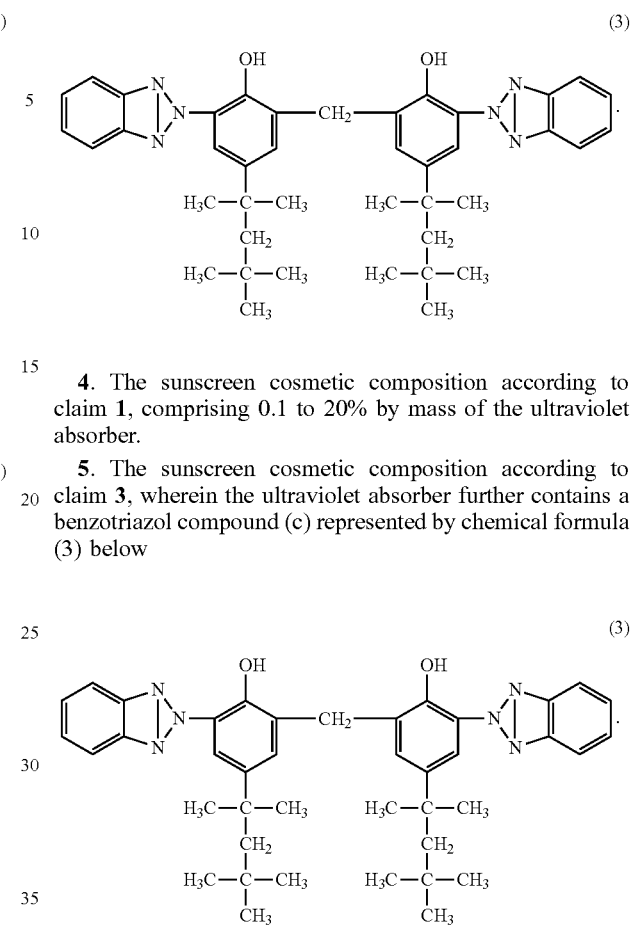

wherein R₁ represents a linear or branched alkyl group with 1 to 12 carbon atoms, and R₂ represents an alkyl group with 1 to 8 carbon atoms;
wherein said composition does not contain water.

2. The sunscreen cosmetic composition according to claim 1, wherein $R_1$ in general formula (1) above is a linear alkyl group with 1 to 12 carbon atoms, and $R_2$ is a methyl group.

3. The sunscreen cosmetic composition according to claim 1, wherein the ultraviolet absorber further contains a benzotriazol compound (c) represented by chemical formula (3) below 4. The sunscreen cosmetic composition according to claim 1, comprising 0.1 to 20% by mass of the ultraviolet absorber.

5. The sunscreen cosmetic composition according to claim 3, wherein the ultraviolet absorber further contains a benzotriazol compound (c) represented by chemical formula (3) below 6. The sunscreen cosmetic composition according to claim 2, comprising 0.1 to 20% by mass of the ultraviolet absorber.

7. The sunscreen cosmetic composition according to claim 3, comprising 0.1 to 20% by mass of the ultraviolet absorber.

* * * * *